United States Patent
Wnendt et al.

(10) Patent No.: US 6,476,044 B1
(45) Date of Patent: Nov. 5, 2002

(54) USE OF MORPHINE DERIVATIVES AS MEDICAMENTS FOR THE TREATMENT OF NEUROPATHIC PROBLEMS

(75) Inventors: Stephan Wnendt, Aachen; Wolfgang Strassburger, Wuerselen; Helmut Buschmann, Aachen; Elke Reiss-Mueller, Bielefeld; Thomas Krueger, Langerwehe-Schlich, all of (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/076,109

(22) Filed: Feb. 15, 2002

Related U.S. Application Data

(63) Continuation of application No. PCT/EP00/07585, filed on Aug. 4, 2000.

(51) Int. Cl.$^7$ ............................................. A61K 31/44
(52) U.S. Cl. ...................................................... 514/282
(58) Field of Search ........................................... 514/282

(56) References Cited

FOREIGN PATENT DOCUMENTS

| WO | WO 95/31463 | * 11/1995 |
| WO | WO 98/22467 | * 5/1998 |

* cited by examiner

*Primary Examiner*—Raymond Henley, III
(74) *Attorney, Agent, or Firm*—Crowell & Moring LLP

(57) ABSTRACT

A method for agonizing or antagonizing the ORL1 (opioid receptor-like) receptor of the nociceptin/orphanin FQ ligand ORL1 receptor system using a morphinan compound of the general formula I or derivatives thereof. Also disclosed are methods for treating neuropathic pain and/or anxiolysis and/or depression and/or diuresis and/or urinary incontinence and/or hypotension and or hypertension and/or senile dementia and/or Alzheimer's disease and/or general cognitive disfunctions an/or tinnitus and/or impaired hearing and/or epilepsy and/or obesity and/or cachexia.

13 Claims, No Drawings

USE OF MORPHINE DERIVATIVES AS MEDICAMENTS FOR THE TREATMENT OF NEUROPATHIC PROBLEMS

CROSS REFERENCE TO RELATED APPLICATIONS

The present application is a continuation of international patent application no. PCT/EP00/07585, filed Aug. 4, 2000, designating the United States of America, the entire disclosure of which is incorporated herein by reference. Priority is claimed based on Federal Republic of Germany patent application no. 199 39 044.4, filed Aug. 18, 1999.

BACKGROUND AND SUMMARY OF THE INVENTION

The present invention relates to the use of morphinan derivatives as well as their bases or salts of physiologically compatible acids as regulators for the nociceptin/orphanin FQ ligand ORL1 receptor system and for the production of a medicament.

The heptadecapeptide nociceptin/orphanin FQ is an endogenous ligand of the ORL1 (opioid receptor-like) receptor (Meunier et al., Nature 377, 1995, pp. 532–535) that belongs to the family of opioid receptors and can be found in many regions of the brain and spinal cord (Mollereau et al., FEBS Letters, 341, 1994, pp. 33–38, Darland et al., Trends in Neurosciences, 21, 1998, pp. 215–221). The peptide is characterised by a high affinity, with a Kd value of around 56 pM (Ardati et al., Mol. Pharmacol. 51, pp. 816–824), and by a high selectivity for the ORL1 receptor. The ORL1 receptor is homologous to the $\mu$, $\kappa$ and $\delta$ opioid receptors, and the amino acid sequence of the nociceptin/orphanin FQ peptide has a strong similarity to those of the known opioid peptides. The activation of the receptor induced by nociceptin/orphanin FQ leads via the coupling with $G_{i/o}$ proteins to an inhibition of adenylate cyclase (Meunier et al., Nature 377, 1995, pp. 532–535). Also, at the cellular level there are functional similarities between the $\mu$, $\kappa$ and $\delta$ opioid receptors and the ORL1 receptor as regards the activation of the potassium channel (Matthes et al., Mo. Pharmacol. 50, 1996, pp. 447–450; Vaughan et al., Br. J. Pharmacol. 117, 1996, pp. 1609–1611) and the inhibition of the L, N and P/Q type calcium channels (Conner et al., Br. J. Pharmacol. 118, 1996, pp. 205–207; Knoflach et al., J. Neuroscience 16, 1996, pp. 6657–6664).

The nociceptin/orphanin FQ peptide exhibits after intercerebroventricular application a pronociceptive and hyperalgesic activity in various animal models (Reinscheid et al., Science 270, 1995, pp. 792–794; Hara et al., Br. J. Pharmacol. 121, 1997, pp. 401–408). These results may be explained as inhibition of stress-induced analgesia (Mogil et al., Neurosci. Letters 214, 1996, pp. 131–134, as well as Neuroscience 75, 1996, pp. 333–337). In this connection an anxiolytic activity of the nociceptin/orphanin FQ peptide was also detected (Jenck et al., Proc. Natl. Acad. Sci. USA 94, 1997, 14854–14858).

On the other hand an antinociceptive effect of nociceptin/orphanin FQ, in particular after intrathecal application, was also found in various animal models. Nociceptin/orphanin FQ inhibits the activity of kainate-stimulated or glutamate-stimulated posterior root ganglioneurons (Shu et al., Neuropeptides, 32, 1998, 567–571) or glutamate-stimulated spinal cord neurons (Faber et al., Br. J. Pharmacol., 119, 1996, pp. 189–190); nociceptin/orphanin FQ has an antinociceptive action in the tail-flick test in mice (King et al., Neurosci. Lett., 223, 1997, 113–116), in the flexor-reflex model in rats (Xu et al., NeuroReport, 7, 1996, 2092–2094) and in the formalin test in rats (Yamamoto et al., Neuroscience, 81, 1997, pp. 249–254). An antinociceptive effect of nociceptin/orphanin FQ was also detected in neuropathic pain models (Yamamoto and Nozaki-Taguchi, Anesthesiology, 87, 1997), which is all the more interesting in that the efficacy of nociceptin/orphanin FQ increases after axotomy of spinal nerves. This is in contrast to conventional opioids, whose efficacy decreases under these conditions (Abdulla and Smith, J. Neurosci., 18, 1998, pp. 9685–9694).

The nociceptin/orphanin FQ ligand ORL1 receptor system is also involved in the regulation of further physiological and pathophysiological processes. These include, inter alia, learning and the formation of memory (Sandin et al., European. J. Neurosci., 9, 1997, pp. 194–197; Manabe et al., Nature, 394, 1997, pp. 577–581), auditory perception (Nishi et al., EMBO J., 16, 1997, pp. 1858–1864), food intake (Pomonis et al., NeuroReport, 8, 1996, pp. 369–371), blood pressure regulation (Gumusel et al., Life Sci., 60, 1997, pp. 141–145; Campion and Kadowitz, Biochem. Biophys. Res. Comm., 234, 1997, pp. 309–312), epilepsy (Gutierrez et al., Abstract 536.18, Society for Neuroscience, Vol. 24, 28$^{th}$ Ann. Meeting, Los Angeles, Nov. 7–12, 1998) and diuresis (Kapista et al., Life Sciences, 60, 1997, PL 15–21).

Morphinan derivatives as well as processes for their production are known from WO 98/22467, WO 95/31463 and WO 95/31464. These compounds are described as $\delta$-selective opioid agonists and opioid antagonists for the treatment of conditions such as for example shock, constipation, mental disorders, eating disorders, injury to the central nervous system, alcoholism and immune function disorders.

The object of the present invention was to provide medicaments that act on the nociceptin/orphanin FQ ligand ORL1 receptor system and are thus suitable for treating neuropathic pain and/or anxiolysis and/or depression and/or diuresis and/or urinary incontinence and/or hypotension and or hypertension and/or senile dementia and/or Alzheimer's disease and/or general cognitive dysfunctions and/or tinnitus and/or impaired hearing and/or epilepsy and/or obesity and/or cachexia.

DETAILED DESCRIPTION OF THE INVENTION

It has now surprisingly been found that morphinan derivatives of the following general formula I exert an influence on the control of various physiological and pathophysiological processes in which the nociceptin/ orphanin FQ ligand ORL1 receptor system is involved. The aforementioned processes include, inter alia, the sensation of neuropathic pain, anxiety behavior, learning and memory formation, blood pressure regulation, hearing, food intake, epilepsy and diuresis.

The present invention accordingly provides for the use of morphinan derivatives of the general formula I

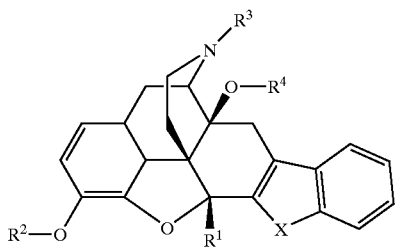

I wherein

R¹ denotes H, a $C_{1-4}$ alkyl radical or a $C_{2-4}$ alkenyl radical,

R² denotes H, a $C_{1-18}$ alkyl radical, preferably a $C_{1-10}$ alkyl radical, a $C_{2-18}$ alkenyl radical, preferably a $C_{2-10}$ alkenyl radical, a heterocyclyl radical or an aryl radical, R³ denotes a $C_{1-18}$ alkyl radical, preferably a $C_{1-10}$ alkyl radical, a $C_{2-18}$ alkenyl radical, preferably a $C_{2-10}$ alkenyl radical, a $C_{3-7}$ cycloalkyl, aryl or heterocyclyl radical bound via a $C_{1-4}$ alkylene group, or a $C_{3-7}$ cycloalkyl, aryl or heterocyclyl radical bound via a $C_{2-4}$ alkenylene group, R⁴ denotes H, a $C_{1-18}$ alkyl radical, preferably a $C_{1-10}$ alkyl radical, a $C_{2-18}$ alkenyl radical, preferably a $C_{2-10}$ alkenyl radical, a $C_{3-7}$ cycloalkyl or aryl radical bound via a $C_{1-4}$ alkylene group, or a $C_{3-7}$ cycloalkyl or aryl radical bound via a $C_{2-4}$ alkenylene group, and X denotes O or NR⁵ where R⁵ denotes H, a $C_{1-18}$ alkyl radical, preferably a $C_{1-10}$ alkyl radical, a $C_{2-18}$ alkenyl radical, preferably a $C_{2-10}$ alkenyl radical, a $C_{3-7}$ cycloalkyl, aryl or heterocyclyl radical bound via a $C_{1-4}$ alkylene group, or a $C_{3-7}$ cycloalkyl, aryl or heterocyclyl radical bound via a $C_{2-4}$ alkenylene group, and/or their enantiomers, diastereomers, or physiologically compatible salts, as regulators for the nociceptin/orphanin FQ ligand ORL1 receptor system.

The term alkyl radicals also includes hydrocarbons at least singly substituted preferably by halogen, particularly preferably by fluorine. If these contain one or more substituents, then the latter may be identical or different. Preferably the alkyl radicals are methyl, ethyl, propyl, 1-methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, heptyl, nonyl or decanyl.

The term alkenyl radicals also includes hydrocarbons that contain at least one double bond, and may be at least singly substituted, preferably by halogen, particularly preferably by fluorine. If the alkenyl radical contains more than one substituent, then these may be identical or different. Preferably the alkenyl radicals are 2-propenyl, 2-butenyl, 1-methyl-2-propenyl or 2-methyl-2-propenyl.

The term aryl radical also includes phenyl or naphthyl radicals at least singly substituted by an OH, a halogen, preferably F and/or Cl, a $CF_3$, a $C_{1-6}$ alkyl, a $C_{1-6}$ alkoxy, a $C_{1-7}$ cycloalkoxy, a $C_{3-7}$ cycloalkyl, a $C_{2-6}$ alkylene or phenyl radical. The phenyl radicals may also be condensed with further rings.

The term heterocyclyl radical is understood to include saturated as well as unsaturated heterocyclic compounds, preferably 5–7-membered heterocyclic compounds that contain at least one heteroatom, preferably nitrogen, oxygen and/or sulfur, particularly preferably nitrogen and/or oxy-gen. Preferably the saturated heterocyclics are 1,4-dioxane, tetrahydrofuran or 1,4-thioxane. Preferably the unsaturated heterocyclics are furan, thiophene, pyridine, pyrimidine, thiazole, oxazole, isoxazole, pyridazine, pyrazine, quinoline, isoquinoline, phthalazine or quinazoline.

Preferred are morphinan derivatives of the general formula I in which R¹ denotes H or a $C_{1-4}$ alkyl radical; R² denotes H or a $C_{1-4}$ alkyl radical; R³ denotes a $C_{1-4}$ alkyl radical or a $C_{2-4}$ alkenyl radical; R⁴ denotes H, a $C_{1-4}$ alkyl radical, a $C_{3-7}$ cycloalkyl or aryl radical bound via a $C_{1-4}$ alkylene group; and X denotes NR⁵ wherein R⁵ denotes a $C_{1-10}$ alkyl, a $C_{2-10}$ alkenyl, a $C_{3-7}$ cycloalkyl or aryl radical bound via a $C_{1-4}$ alkylene group, or a $C_{3-7}$ cycloalkyl or aryl radical bound via a $C_{2-4}$ alkenylene group.

Also preferred are morphinan derivatives of the general formula I in which R¹ denotes H or a $C_{1-4}$ alkyl radical; R² denotes H; R³ denotes a $C_{1-4}$ alkyl radical or a $C_{2-4}$ alkenyl radical; R⁴ denotes H, a $C_{1-4}$ alkyl radical or a $C_{3-7}$ cycloalkyl or aryl radical bound via a $C_{1-4}$ alkylene group; and X denotes NR⁵ wherein R⁵ denotes a $C_{2-10}$ alkenyl radical, a $C_{3-7}$ cycloalkyl or aryl radical bound via a $C_{1-4}$ alkylene group, or an aryl radical bound via a $C_{2-4}$ alkenylene group.

Particularly preferred are morphinan derivatives of the general formula I in which R¹ denotes H, R² denotes H, R³ denotes a $C_{2-4}$ alkenyl radical, R⁴ denotes H and X denotes NR⁵, wherein R⁵ denotes an aryl radical bound via a $C_{1-4}$ alkylene group or an aryl radical bound via a $C_{2-4}$ alkenylene group.

Particularly preferred are the following morphinan derivatives:

17-allyl-6,7-didehydro-4,5α-epoxy-3,14-dihydroxy-1'-(o-chlorobenzyl)indolo[6,7:2,'3']-morphinan hydrochloride, 17-allyl-6,7-didehydro-4,5α-epoxy-3-hydroxy-14-(m-chloro-methoxyphenyl)1'-(m-chlorobenzyl)indolo[6,7:2,'3']-morphinan hydrochloride, or 17-cyclopropylmethyl-6,7-didehydro-4,5α-epoxy-3-hydroxy-14-(o-chloromethoxyphenyl) 1'-(o-chlorobenzyl)indolo[6,7:2,'3']-morphinan hydrochloride as ORL1 receptor antagonists, and 17-cyclopropylmethyl-6,7-didehydro-4,5α-epoxy-3-hydroxy-14-(methoxynaphthalene)1'-(β-methylnaphthalene)indolo-[6,7:2,'3']-morphinan hydrochloride or 17-cyclopropylmethyl-6,7-didehydro-4,5α-epoxy-14-hydroxy-3-benzyloxy-1'-(p-methoxycarbonylmethylphenyl)-indolo[6,7:2,'3']-morphinan hydrochloride as ORL1 receptor agonist.

The present invention also provides for a medicament and a method for treating neuropathic pain and/or anxiolysis and/or depression and/or diuresis and/or urinary incontinence and/or hypotension and or hypertension and/or senile dementia and/or Alzheimer's disease and/or general cognitive dysfunctions and/or tinnitus and/or impaired hearing and/or epilepsy and/or obesity and/or cachexia using the morphinan derivatives of the general formula I as regulators for the nociceptin/orphanin FQ ligand ORL1 receptor system.

The present invention furthermore provides a method and a medicament for treating neuropathic pain and/or anxiolysis and/or depression and/or diuresis and/or urinary incontinence and/or hypotension and or hypertension and/or senile dementia and/or Alzheimer's disease and/or general cognitive dysfunctions and/or tinnitus and/or impaired hearing and/or epilepsy and/or obesity and/or cachexia using the morphinan derivatives of the general formula I.

For the preparation of the corresponding pharmaceutical formulations, in addition to at least one morphinan derivative of the formula I there are also used carrier materials, or excipients, such as fillers, solvents, diluents, colourants and/or binders. The choice of the auxiliary substances as well as the amounts thereof to be used depends on whether the medicament, or pharmaceutical composition, is to be administered orally, intravenously, intraperitoneally, intradermally, intramuscularly, intranasally, buccally or topically. For oral application preparations in the form of tablets, sugar-coated pills, capsules, granules, drops, juices and syrups are suitable, while for parenteral, topical and inhalative administration, solutions, suspensions, easily reconstitutable dry preparations as well as sprays are suitable. Compounds of the formula I according to the invention in a depot form, in dissolved form or in a plaster, optionally with the addition of agents promoting penetration of the skin, are suitable percutaneous application preparations. Orally or percutaneously usable preparation forms can provide for the delayed release of the compounds of the formula I according to the invention.

The amount of active constituent to be administered to the patient varies depending on the patient's weight, type of application, medical indications and severity of the condition. Normally 0.1 to 1 mg/kg body weight of at least one morphinan derivative of the formula I is administered.

Molecular Pharmacology Investigations

The morphinan derivatives of the general formula I according to the invention were identified with a reporter gene system as ORL1 receptor agonists or as ORL1 receptor antagonists. This reporter gene system is based on the expression of the human ORL1 receptor in CHO-K1 cells, which carry a cAMP-sensitive luciferase gene (Wnendt et al., Regulatory Peptides, 80, 1999, p. 127 the entire disclosure of which is incorporated herein by reference). The formation of cAMP is induced by forskolin, an adenylate cyclase activator. Since the ORL1 receptor in the binding of the natural ligand nociceptin/orphanin FQ reduces the formation of cAMP by inhibiting adenylate cyclase, the effect of a substance as agonist or antagonist on the ORL receptor can be detected by a change in the cAMP-dependent luciferase formation.

ORL1 receptor agonists have the same effect as the natural ligand nociceptin/orphanin FQ. Also, they inhibit in a concentration-dependent manner luciferase formation due to the binding to the ORL1 receptor. The potency, expressed as the $IC_{50}$ value, indicates the concentration at which the semi-maximum effect of the agonist is reached.

The ORL1 receptor antagonists compete with the natural ligand nociceptin/orphanin FQ for the binding to the ORL1 receptor. The inhibition of luciferase formation due to the agonists is lifted to the extent that the antagonist binds to the ORL1 receptor. The dose-effect curve of the natural ligand nociceptin/orphanin FQ is displaced to higher concentration ranges. The effect of the antagonists is described by the $pK_B$ value. This logarithmic quantity indicates the concentration at which the potency of the natural ligand nociceptin/orphanin FQ is reduced by a factor of 2 (Kenakin, T., Pharmacological Analysis of Drug-Receptor Interaction, 3rd Edition, Lippincott-Raven, 1997, Philadelphia, New York).

The reporter gene system was constructed as follows:

A cDNA coding for the ORL1 receptor was cloned using standard methods from THP-1 cells (European Cell Culture Collection, Porton Down, Great Britain) of a human monocyte cell line and integrated into the plasmid pZeoSV (Invitrogen, Leek, Netherlands). This plasmid, pZeoORL17, was used for the transfection of a cell line, CHO-K1/pSE66/K9, that contains the cAMP reporter plasmid pSE66. The plasmid pSE66 was constructed on the basis of the plasmid pMAMneo-LUC (Clontech, Palo Alto, Calif.) by replacing the RSV promoter of this plasmid by a promoter region in which six CRE elements (cAMP-responsive elements, Comb et al., Nature, 323, 1986, pp. 353–356; Montminy et al., Proc. Natl. Acad. Sci. USA, 83, 1986, pp. 6682–6686; Short et al., J. Biol. Chem., 261, 1986, pp. 9721–9726) lie upstream of a promoter. The SV40 promoter derives from the plasmid pGL2-promoter (Promega, Madison, Wis.). The promoter region constructed in this way controls in the plasmid pSE66 the expression of the luciferase gene from pMAMneo-LUC. Furthermore, pSE66 carries a G418 resistance gene under the control of a further SV40 promoter. The cell line CHO-K1 (European Cell Culture Collection, Porton Down, Great Britain) was rendered stable with pSE66 and the clone CHO-K1/pSE66/K9 was selected for the transfection with pZeoORL17. Monoclonal pZeoORL17-tranformants were selected in the nutrient mixture F-12 (Ham) with glutamine (Gibco-BRL, Weiterstadt, Germany), amplified with 50 µg/ml of G418 (Gibco-BRL, Weiterstadt, Germany) and 200 µg/ml of zeocin (Invitrogen, Leek, Netherldands).

Nociceptin/orphanin FQ sensitive clones were identified by incubating in each case 20,000 cells of a clone in a 96-well microtiter plate in a volume of 100 µl for 6 hours with 1 µM forskolin (RBI, Deisenhofen, Germany) in the presence or absence of 10 µM of nociceptin/orphanin FQ, and were then measured using the luciferase detection kit (Roche, Mannheim, Germany) (Ford and Leach, Methods in Molecular Biology, 102, 1998, pp. 3–20).

The clone CHO-K1/pSE66/K9/pZeoORL17/K21 was selected for the analysis of test compounds, the test compounds being dissolved in dimethyl sulfoxide and the end concentration of dimethyl sulfoxide being set at 1% (v/v). The antagonist test was carried out in the presence of 10 nM of nociceptin/orphanin FQ.

Furthermore a receptor binding assay with $^3$H-nociceptin/orphanin FQ was carried out with the compounds according to the invention using membranes of recombinant CHO-ORL1 cells. This test system was implemented according to the method proposed by Ardati et al. (Mol. Pharmacol., 51, 1997, pp. 816–824). The concentration of $^3$H-N/OFQ in these experiments was 0.5 nM. The binding assays were performed in each case with 20 µg of membrane protein per 200 µl of batch in 50 mM of Hepes, pH 7.4, 10 mM $MgCl_2$ and 1 mM EDTA. The binding to the ORL1 receptor was determined using in each case 1 mg of WGA-SPA beads (Amersham-Pharmacia, Freiburg) by incubating the batch for one hour at room temperature followed by measurement in a Trilux scintillation counter (Wallac, Finland). The affinity is given as the $K_i$ value.

The production of the morphinan derivatives of the general formula I is described in WO 95/31463 and WO 95/31464, the disclosures of which are incorporated herein by reference in their entirety.

EXAMPLES

The following examples serve to illustrate the invention without however restricting the general inventive concept.

Example 1

Agonistic or Antagonistic Effect of Exemplary Compounds on ORL1 Receptor

For each of these exemplary compounds 1 to 7 the agonistic or antagonistic effect on the ORL1 receptor was determined according to the specified molecular pharmacology investigations. The corresponding $IC_{50}$ and $pK_B$ values are given in Table 1.

TABLE 1

| Example | ORL1 Antagonists | PKB ORL1 Reporter Gene Assay | $IC_{50}$ (nM) ORL1 Reporter Gene Assay | Ki (nM) ORL1 Binding Assay |
|---|---|---|---|---|
| 1 | 17-allyl-6,7-didehydro-4,5α-epoxy-3,14-dihydroxy-1'-(o-chlorobenzyl)indolo-[6,7:2,'3']-morphinan hydrochloride | 7.37 | | 449 |
| 2 | 17-allyl-6,7-didehydro-4,5α-epoxy-3-hydroxy-14-(m-chloromethoxyphenyl)1'-(m-chlorobenzyl)indolo[6,7:2,'3']-morphinan hydrochloride | 6.99 | | 1079 |
| 3 | 17-cyclopropylmethyl-6,7-didehydro-4,5α-epoxy-3-hydroxy-14-(o-chloromethoxyphenyl)1'-(o-chlorobenzyl)-indolo[6,7:2,'3']-morphinan hydrochloride | 6.39 | | 718 |
| 4 | 17-cyclopropylmethyl-6,7-didehydro-4,5α-epoxy-3-hydroxy-14-(methoxynaphthalene)1'-(β-methylnaphthalene)indolo-[6,7:2,'3']-morphinan hydrochloride | | 31.2 | 982 |
| 5 | 17-cyclopropylmethyl-6,7-didehydro-4,5α-epoxy-14-hydroxy-3-benzyloxy-1'-(p-methoxycarbonylmethylphenyl)-indolo-[6,7:2,'3']-morphinan hydrochloride | | 25.8 | Not measured |

Example II

Synthesis of Morphinan Derivatives of Formula I

The morphinan derivatives of the general formula I have been synthesised by the following methods:

By treating thebaine of the formula II

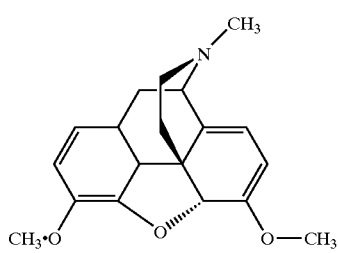

with dialkyl sulfates, fluorosulfonic acid alkyl esters, alkylsulfonic acid alkyl esters, arylsulfonic acid alkyl esters, alkyl halides, arylalkyl halides, alkylsulfonic acid aryl esters, arylsulfonic acid aryl esters, arylalkenyl halides or chloroformates in solvents such as tetrahydrofuran or diethyl ether using a strong base such as n-butyl lithium, lithium diethylamide or lithium diisopropylamide at low temperatures (−20° to −80° C.), compounds of the formula III could be obtained (Boden et al., J. Organic. Chem. 1982, 47, 1347–1349; H. Schmidhammer et al., Helv. Chim. Acta 1988, 71, 642–647, the disclosures of which are incorporated herein by reference),

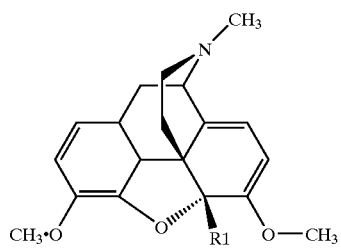

wherein $R^1$ denotes H, a $C_{1-4}$ alkyl radical or a $C_{2-4}$ alkenyl radical.

By reacting substituted thebaine derivatives of the formula III with performic acid or m-chloroperbenzoic acid at temperatures between 0° and 60° C., the hydroxycodeinone derivatives of the formula IV could be obtained (H. Schmidhammer et al., Helv. Chim. Acta 1988, 71, 1801–1804, the disclosure of which is incorporated herein by reference).

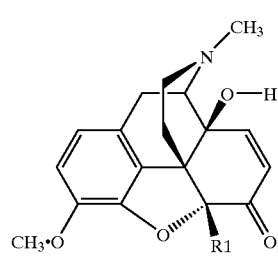

By treating the hydroxycodeinone derivatives of the formula IV with dialkyl sulfates, alkyl halides, cycloalkyl halides, cycloalkylalkenyl halides, alkenyl halides, arylalkyl halides, arylalkenyl halides or chloroformates in solvents such as N,N-dimethylformamide or tetrahydrofuran using strong bases such as sodium hydride or potassium hydride, compounds of the formula V could be produced,

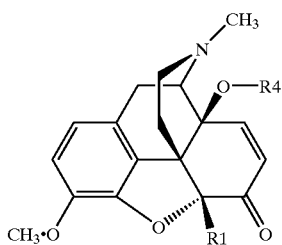

V wherein $R^1$ has the meaning as in formula III above and $R^4$ denotes a $C_{1-18}$ alkyl, preferably a $C_{1-10}$ alkyl radical, a $C_{2-18}$ alkenyl, preferably a $C_{2-10}$ alkenyl radical, a $C_{3-7}$ cycloalkyl or aryl radical bound via a $C_{1-4}$ alkylene group, or a $C_{3-7}$ cycloalkyl or aryl radical bound via a $C_{2-4}$ alkenylene group.

By catalytic hydrogenation using catalysts such as palladium on active charcoal in solvents such as methanol, ethanol or glacial acetic acid, the compounds of the formula V could be converted into compounds of the formula VI,

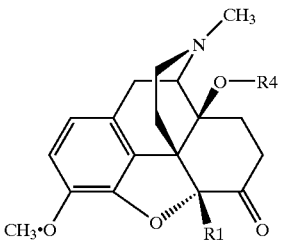

VI wherein $R^1$ denotes H, a $C_{1-4}$ alkyl or a $C_{2-4}$ alkenyl radical, and $R^4$ denotes a $C_{1-18}$ alkyl, preferably a $C_{1-10}$ alkyl radical, a $C_{2-18}$ alkenyl, preferably a $C_{2-10}$ alkenyl radical, a $C_{3-7}$ cycloalkyl or aryl radical bound via a $C_{1-4}$ alkylene group, or a $C_{3-7}$ cycloalkyl or aryl radical bound via a $C_{2-4}$ alkenylene group.

Compounds of the formula VII could be obtained in a manner well-known to an ordinarily skilled person in the art from compounds of the formula VI by N-demethylation, preferably using chloroformates, followed by reductive addition,

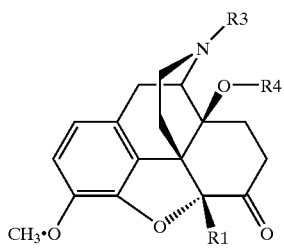

VII wherein $R^1$ and $R^4$ have the meanings as in formula VI above and $R^3$ denotes a $C_{1-18}$ s alkyl, preferably a $C_{1-10}$ alkyl radical, a $C_{2-18}$ alkenyl, preferably a $C_{2-10}$ alkenyl radical, a $C_{3-7}$ cycloalkyl, aryl or heterocyclyl radical bound via a $C_{1-4}$ alkylene group, or a $C_{3-7}$ cycloalkyl, aryl or heterocyclyl radical bound via a $C_{2-4}$ alkenylene group.

Substances of the Formula VIII

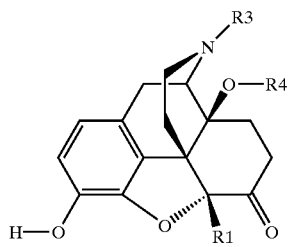

VIII wherein $R^1$, $R^3$ and $R^4$ have the meanings as in formula VII were obtained by ether cleavage using boron tribromide in solvents such as dichloromethane or chloroform at temperatures between −10° and +10° C., or by heating under reflux in 48% hydrobromic acid or by using other ether cleavage reagents well-known to an ordinarily skilled person.

By reacting the phenolic hydroxyl group of Formula VIII function with bases such as sodium hydride in solvents such as tetrahydrofuran or N,N-dimethylformamide followed by addition of alkyl halides, alkenyl halides, heterocyclyl halides or aryl halides, compounds of the formula IX could be obtained (H. Schmidhammer et al., J. Med. Chem. 1995, 38, 3071–3077 which is incorporated herein by reference in its entirety),

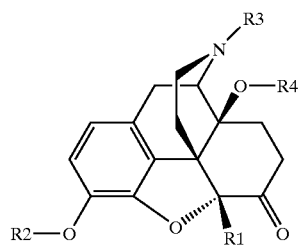

IX wherein $R^1$, $R^3$ and $R^4$ have the meanings as in formula VII and $R^2$ denotes a $C_{1-18}$ alkyl preferably a $C_{1-10}$ alkyl radical, a $C_{2-18}$ alkenyl, preferably a $C_{2-10}$ alkenyl radical, a heterocyclyl or aryl radical.

Compounds of the formula IX could be converted by reaction with phenylhydrazine hydrochloride in the presence of an acid, preferably using methanesulfonic acid, sulfuric acid or hydrochloric acid, within the meaning of the Fischer indole synthesis, into compounds of the general formula I in which X denotes NH and the remaining radicals $R^1$ to $R^4$ have the meanings as in formula IX (P.S. Porthogese et al., J. Med. Chem. 1988, 31, 281–282, H. Schmidhammer et al., J. Med. Chem. 1990, 33, 1200–1206, which are both incorporated herein by reference).

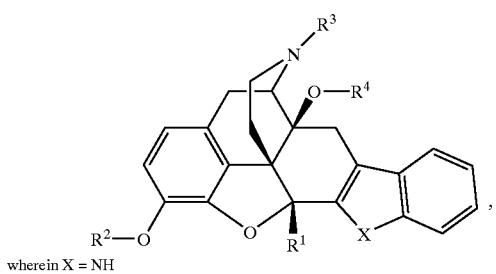

wherein X = NH

Compounds of the general formula I wherein X denotes NR⁵ could be obtained either by condensing compounds of the formula IX with Boc-protected N-substituted N-phenylhydrazines of the formula X, preferably by heating under reflux in methanolic hydrochloric acid (P.S. Porthogese et al., J. Med. Chem. 1994, 37, 1882–1885), or in a manner well-known in the art by addition reactions starting from compounds of the formula I wherein X denotes NH.

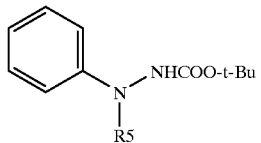

Compounds of the formula IX could be converted by reaction with O-phenylhydroxylamine hydrochloride in the presence of an acid, preferably methanesulfonic acid, sulfuric acid or hydrochloric acid, into compounds of the general formula I wherein X denotes O, and the remaining radicals $R^1$ to $R^4$ have the meanings as in formula IX (P.S. Porthogese et al., J. Med. Chem. 1988, 31, 281–282).

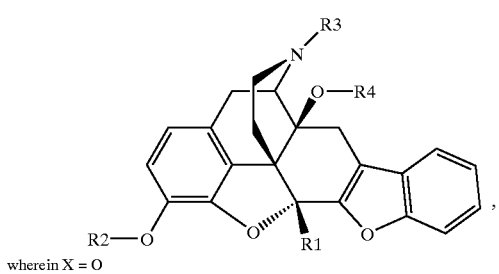

wherein X = O

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A method for agonizing or antagonizing the ORL1 (opioid receptor-like) receptor of the nociceptin/orphanin FQ ligand ORL1 receptor system, the method comprising administering, to a cell comprising said receptor system, an effective amount of a composition comprising a morphinan compound of formula I:

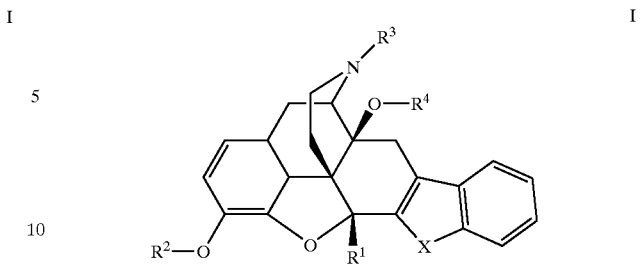

wherein
$R^1$ denotes H, a $C_{1-4}$ alkyl group or a $C_{2-4}$ alkenyl group;
$R^2$ denotes H, a $C_{1-18}$ alkyl group, a $C_{2-18}$ alkenyl group, a heterocyclyl group or an aryl group;
$R^3$ denotes a $C_{1-18}$ alkyl group, a $C_{2-18}$ alkenyl group, a $C_{3-7}$ cycloalkyl, aryl or heterocyclyl group bound via a $C_{1-4}$ alkylene group, or a $C_{3-7}$ cycloalkyl, aryl or heterocyclyl group bound via a $C_{2-4}$ alkenylene group;
$R^4$ denotes H, a $C_{1-18}$ alkyl group, a $C_{2-18}$ alkenyl group, a $C_{3-7}$ cycloalkyl or aryl group bound via a $C_{1-4}$ alkylene group, or a $C_{3-7}$ cycloalkyl or aryl group bound via a $C_{2-4}$ alkenylene group, and
X denotes O or $NR^5$ where
$R^5$ denotes H, a $C_{1-18}$ alkyl group, a $C_{2-18}$ alkenyl group, a $C_{3-7}$ cycloalkyl, aryl or heterocyclyl group bound via a $C_{1-4}$ alkylene group, or a $C_{3-7}$ cycloalkyl, aryl or heterocyclyl group bound via a $C_{2-4}$ alkenylene group,
or an enantiomer, diastereomer, or physiologically compatible salt thereof.

2. A method according to claim 1, wherein $R^2$ denotes a $C_{1-10}$ alkyl group.

3. A method according to claim 1, wherein $R^2$ denotes a $C_{2-10}$ alkenyl group.

4. A method according to claim 1, wherein $R^3$ denotes a $C_{1-10}$ alkyl group.

5. A method according to claim 1, wherein $R^3$ denotes a $C_{2-10}$ alkenyl group.

6. A method according to claim 1, wherein $R^4$ denotes H a $C_{1-10}$ alkyl group.

7. A method according to claim 1, wherein $R^4$ denotes a $C_{2-10}$ alkenyl group.

8. A method according to claim 1, wherein $R^5$ denotes a $C_{1-10}$ alkyl group.

9. A method according to claim 1, wherein $R^5$ denotes a $C_{2-10}$ alkenyl group.

10. A method for antagonizing the ORL1 receptor of the nociceptin/orphanin FQ ligand ORL1 receptor system according to claim 1, wherein the morphinan compound is:
17-allyl-6,7-didehydro-4,5α-epoxy-3,14-dihydroxy-1'-(o-chlorobenzyl)indolo[6,7:2,'3']-morphinan hydrochloride,
17-allyl-6,7-didehydro-4,5α-epoxy-3-hydroxy-14-(m-chloro-methoxyphenyl)1'-(m-chlorobenzyl)indolo[6,7:2,'3']-morphinan hydrochloride, or
17-cyclopropylmethyl-6,7-didehydro-4,5α-epoxy-3-hydroxy-14-(o-chloromethoxyphenyl)1'-(o-chlorobenzyl)indolo[6,7:2,'3']-morphinan hydrochloride.

11. A method for agonizing the ORL1 receptor of the nociceptin/orphanin FQ ligand ORL1 receptor system according to claim 1, wherein the morphinan compound is:
17-cyclopropylmethyl-6,7-didehydro-4,5α-epoxy-3-hydroxy-14-(methoxynaphthalene)1'-(β- methylnaphthalene)indolo-[6,7:2,'3']-morphinan hydrochloride or 17-cyclopropylmethyl-6,7-didehydro-4,5α-epoxy-14-hydroxy-3-benzyloxy-1'-(p-methoxycarbonylmethylphenyl)-indolo[6,7:2,'3']-morphinan hydrochloride.

12. A method for the treatment of at least one condition selected from the group consisting of neuropathic pain, anxiolysis, depression, diuresis, urinary incontinence, hypotension, hypertension, senile dementia, Alzheimer's disease, general cognitive dysfunctions, tinnitus, impaired hearing, epilepsy, obesity, and cachexia, the method comprising administering an effective amount of a compound of formula I:

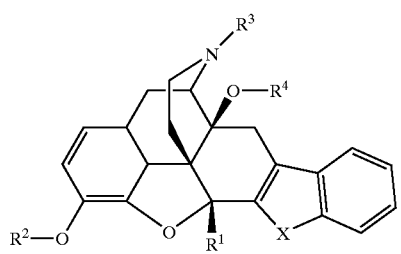

I wherein $R^1$ denotes H, a $C_{1-4}$ alkyl group or a $C_2$ alkenyl group;

$R^2$ denotes H, a $C_{1-18}$ alkyl group, a $C_{2-18}$ alkenyl group, a heterocyclyl group or an aryl group;

$R^3$ denotes a $C_{1-18}$ alkyl group, a $C_{2-18}$ alkenyl group, a $C_{3-7}$ cycloalkyl, aryl or heterocyclyl group bound via a $C_{1-4}$ alkylene group, or a $C_{3-7}$ cycloalkyl, aryl or heterocyclyl group bound via a $C_{2-4}$ alkenylene group;

$R^4$ denotes H, a $C_{1-18}$ alkyl group, a $C_{2-18}$ alkenyl group, preferably a $C_{2-10}$ alkenyl group, a $C_{3-7}$ cycloalkyl or aryl group bound via a $C_{1-4}$ alkylene group, or a $C_{3-7}$ cycloalkyl or aryl group bound via a $C_{2-4}$ alkenylene group, and X denotes O or $NR^5$ where $R^5$ denotes H, a $C_{1-18}$ alkyl group, a $C_{2-18}$ alkenyl group, a $C_{3-7}$ cycloalkyl, aryl or heterocyclyl group bound via a $C_{1-4}$ alkylene group, or a $C_{3-7}$ cycloalkyl, aryl or heterocyclyl group bound via a $C_{2-4}$ alkenylene group, or an enantiomer, diastereomer, or physiologically compatible salt thereof.

13. A method according to claim 12, wherein the morphinan compound is selected from the group consisting of:

17-allyl-6,7-didehydro-4,5α-epoxy-3,14-dihydroxy-1'-(o-chlorobenzyl)indolo[6,7:2,'3']-morphinan hydrochloride;

17-allyl-6,7-didehydro-4,5α-epoxy-3-hydroxy-14-(m-chloro-methoxyphenyl)1'-(m-chlorobenzyl)indolo-[6,7:2,'3']-morphinan hydrochloride;

17-cyclopropylmethyl-6,7-didehydro-4,5α-epoxy-3-hydroxy-14-(o-chloromethoxyphenyl)1'-(o-chlorobenzyl)-indolo[6,7:2,'3']-morphinan hydrochloride;

17-cyclopropylmethyl-6,7-didehydro-4,5α-epoxy-3-hydroxy-14-(methoxynaphthalene)1'-(β-methylnaphthalene)indolo-[6,7:2,'3']-morphinan hydrochloride; and 17-cyclopropylmethyl-6,7-didehydro-4,5α-epoxy-14-hydroxy-3-benzyloxy-1'-(p-methoxycarbonylmethylphenyl)-indolo[6,7:2,'3']-morphinan hydrochloride.

* * * * *